(12) United States Patent
Yano et al.

(10) Patent No.: US 7,180,582 B2
(45) Date of Patent: Feb. 20, 2007

(54) APPARATUS AND METHOD FOR MEASURING CHARACTERISTICS OF OPTICAL FIBERS

(75) Inventors: Tetsuo Yano, Hamamatsu (JP); Emiko Fujiwara, Hamamatsu (JP); Shouichi Aoki, Hamamatsu (JP)

(73) Assignees: Yokogawa Electric Corporation, Tokyo (JP); Ando Electric Co., Ltd., Tokyo (JP)

( * ) Notice: Subject to any disclaimer, the term of this patent is extended or adjusted under 35 U.S.C. 154(b) by 380 days.

(21) Appl. No.: 10/863,883

(22) Filed: Jun. 8, 2004

(65) Prior Publication Data
US 2005/0018174 A1    Jan. 27, 2005

(30) Foreign Application Priority Data
Jul. 24, 2003    (JP)    .............. P. 2003-278744

(51) Int. Cl.
*G01N 21/00*    (2006.01)
(52) U.S. Cl. ........................................... 356/73.1
(58) Field of Classification Search ............ None
See application file for complete search history.

(56) References Cited

U.S. PATENT DOCUMENTS 5,965,874 A * 10/1999 Aso et al. .............. 250/225
6,385,357 B1 * 5/2002 Jopson et al. ............ 385/11
6,462,863 B1 * 10/2002 Atieh et al. ............ 359/337.5

FOREIGN PATENT DOCUMENTS

| JP | 2003-106942 | 4/2003 |
| WO | WO 98/36256 | 8/1998 |

OTHER PUBLICATIONS

Corsi et al., "Beat length characterization based on backscattering analysis in randomly perturbed single-mode fibers," Journal of Lightwave Technology (U.S.), Laser & Electro-Optics Society (LEOS) 17(7):1172-1178 (1999).

(Continued)

*Primary Examiner*—Tu T. Nguyen
(74) *Attorney, Agent, or Firm*—Sughrue Mion, PLLC

(57) ABSTRACT

An apparatus and method for accurate measurement of characteristics of optical fibers (distribution of polarization mode dispersion and distribution of magnitude of birefringence). Pulse light is inputted to a subject optical fiber, back scattered light of the pulse light from the subject optical fiber is detected by a photodetector to find a Stokes vector, and polarization mode dispersion in a longitudinal direction is measured. The apparatus comprises a light source unit for outputting the pulse light having at least three different angular frequencies, and an arithmetic operation unit for calculating the magnitude of linear polarization components and the magnitude of a circular polarization component of a polarization dispersion vector on the basis of the Stokes vector and thus calculating polarization mode dispersion.

13 Claims, 8 Drawing Sheets

OTHER PUBLICATIONS

Corsi et al., "Polarization mode dispersion characterization of single-mode optical fiber using backscattering technique," Journal of Lightwave Technology (U..S.), Laser & Electro-Optics Society (LEOS) 16(10):1832-1843 (1998).

Foschini et al., "Statistical theory of polarization dispersion in single mode fibers," Journal of Lightwave Technology, (U.S.), Laser & Electro-Optics Society (LEOS), 9(11):1439-1456 (1991).

Rogers, "Polarization optical time domain reflectometry," Electronics letters (U.K.), the Institution of Electrical Engineers (IEE) 16(13):489-490 (1980).

Ross, "Birefringence measurement in optical fibers by polarization-optical time-domain reflectometry," Applied Optics (U.S.), Optical Society of America (OSA) 21(19):3489-3495, (1982).

* cited by examiner

APPARATUS AND METHOD FOR MEASURING CHARACTERISTICS OF OPTICAL FIBERS

BACKGROUND OF THE INVENTION

1. Field of the Invention

This invention relates to an apparatus and method for measuring characteristics of optical fibers in which characteristics in the longitudinal direction (distribution of polarization mode dispersion and distribution of magnitude of birefringence) of subject optical fibers are measured, and particularly to an apparatus and method for measuring characteristics of optical fibers that enable accurate measurement of characteristics of optical fibers.

2. Description of the Related Art

Recently, as higher transmission rates are increasingly demanded in the optical communication, transmission rates of 10 Gbps and 40 Gbps are getting realized. However, since dispersions such as material dispersion, waveguide dispersion, multimode dispersion and polarization mode dispersion exist in optical fibers as transmission media, waveform deterioration due to these dispersions is particularly considered to cause troubles. In the case where single-mode optical fibers are used, chromatic dispersion (sum of material dispersion and waveguide dispersion) and polarization mode dispersion are problems. Of these, chromatic dispersion can be compensated relatively easily by dispersion compensating fibers (DCF), reverse dispersion fibers (RDF) having the reverse characteristic of the chromatic dispersion of the single-mode optical fibers, a chromatic dispersion compensator or the like. Many solutions using these fibers or compensator are proposed and generally used.

On the other hand, polarization mode dispersion is caused by various elements such as structural defects of the optical fibers themselves, and elliptic deformation of the core, flexure, stress, and twisting due to manufacturing conditions, construction conditions, use environment and the like. These elements cause birefringence and polarization mode dispersion in the optical fibers. Polarization mode dispersion exists randomly in the optical fibers and changes largely. Therefore, it is difficult to compensate polarization mode dispersion using passive components.

Since compensation by passive components is difficult as described above, it is demanded that seriously defective parts of the already constructed optical fibers should be detected and removed and that defective parts should be detected in the manufacturing process to prevent entry into the markets or the results of measurement of polarization mode dispersion should be fed back to the manufacturing process to lower the proportion of defective parts when manufacturing optical fibers.

To realize detection of defective parts and the like, it is important to measure characteristics in the longitudinal direction of optical fibers and an optical fiber characteristics measuring apparatus is used. Particularly, an optical fiber characteristics measuring apparatus for measuring characteristics of polarization mode dispersion values is called polarization mode dispersion measuring apparatus. To measure this polarization mode dispersion, for example, optical components where polarization modes (polarization states) are orthogonal to each other can be transmitted by a predetermined distance and the time difference $\Delta\tau$ between the optical components generated by the transmission can be found.

A technique of measuring polarization mode dispersion will now be described with reference to FIG. 1. FIG. 1 shows the principle of the conventional measurement of polarization mode dispersion. In FIG. 1, an optical fiber 100 is, for example, a single-mode optical fiber and it is a subject optical fiber. Pulse light having angular frequencies $\omega_1$, $\omega_2$ ($\omega_1 \neq \omega_2$; these angular frequencies are slightly different) is inputted from one end (input side) of the optical fiber 100 and the pulse light transmitted through the optical fiber 100 is received at the other end (output side). On the input side, the pulse light is polarized in different polarization states (for example, 0° and 45° to a reference axis) and thus inputted to the optical fiber 100.

On the output side, the polarization state of the pulse light from the optical fiber 100 is divided into four directions (for example, 0°, 45°, 90°, and circular polarization) and the light intensity in each direction is detected. Stokes vector components (S0, S1, S2, and S3) are found from the light intensity in each direction. Generally, the transmission on the optical fiber 100 is expressed in the form of a Mueller matrix R (orthogonal matrix consisting of three row by three columns). Stokes vectors and Mueller matrix are expressed by the following equations.

$$\hat{S} = R\hat{S}_0$$

$\hat{S}, \hat{S}_0$ represent Stokes vectors $S, S_0$

Since the light intensity of light inputted to the optical fiber 100 is already known, the Mueller matrix R can be found from the Stokes vector $S_0$ of input light on the input side and the Stokes vector S of output light acquired on the output side. The Mueller matrix R is found for each of the angular frequencies $\omega_1$, $\omega_2$.

The Stokes vector S of the output light transmitted through the optical fiber 100 having birefringence is changed by the influence of polarization mode dispersion with respect to changes of the angular frequencies $\omega_1$, $\omega_2$ of the input light. This change is generally expressed by using a vector called polarization dispersion vector $\Omega$ within a polarization state space. The magnitude of the polarization dispersion vector $\Omega$ is equal to polarization mode dispersion. Therefore, the change in the polarization state of the output light based on the changes of the angular frequencies $\omega_1$, $\omega_2$ is expressed by the following known equation (1) using the polarization dispersion vector $\Omega$ and the Mueller matrix R. (See, for example, G. J. Foschini, C. D. Poole, "Statistical theory of polarization dispersion in single mode fibers," JOURNAL OF LIGHTWAVE TECHNOLOGY, (U.S.), Laser & Electro-Optics Society (LEOS), November 1991, vol. 9, (No. 11), pp. 1439–1456.)

$$\frac{d\hat{S}}{d\omega} = \frac{dR}{d\omega}\hat{S}_0 = \frac{dR}{d\omega}R^{-1}\hat{S} = \Omega\hat{S} = \hat{\Omega} \times \hat{S} \quad (1)$$

wherein $$\hat{\Omega} = [\Omega_1 \; \Omega_2 \; \Omega_3]^T \quad \Omega = \begin{pmatrix} 0 & -\Omega_3 & \Omega_2 \\ \Omega_3 & 0 & -\Omega_1 \\ -\Omega_2 & \Omega_1 & 0 \end{pmatrix}$$

$\hat{\Omega}$ represents polarization dispersion vector $\Omega$ and $\Omega$ represents polarization dispersion matrix $\Omega$.

$\Omega_1$, $\Omega_2$ are linear polarization components that are different from each other. $\Omega_3$ is a circular polarization component. The Stokes vector S of the output light is a vector including four components (S0, S1, S2, S3) and the corresponding Mueller matrix R consists of four rows by four columns. However, the S0 component has all the power of the light including non-polarization components. For polarization mode dispersion, changes of light power can be ignored and changes of polarization components alone can be handled. Therefore, the Mueller matrix R is a matrix representing conversion of Stokes vectors in the case where polarization components are normalized and expressed in the form of Poincare' sphere. The Mueller matrix R thus consists of three rows by three columns, omitting the S0 component. Polarization mode dispersion is measured in the polarization state in independent four directions and the S0 component is deducted.

However, in the structure shown in FIG. 1, only polarization mode dispersion on the output end of the optical fiber 100 can be measured. Thus, unidirectional measurement using optical time domain reflectometry (hereinafter referred to as OTDR), which is a known technique, is used to measure the distribution in the longitudinal direction. (See, for example, JP-A-2003-106942, paragraphs No. 0024 to No. 0066 and FIGS. 1 to 9; JP-T-2000-510246 (the term "JP-T" as used herein means a published Japanese translation of a PCT application) and A. J. Rogers, "Polarization optical time domain reflectometry," Electronics letters (U.K.), the Institution of Electrical Engineers (IEE), 1980, Vol. 16, No. 13, pp. 489–490.)

In this OTDR technique, short pulse light is inputted and back scattered light of this pulse light is measured, thereby measuring the characteristics of the optical fiber and also measuring the reflection position from the time taken for the back scattered light to return.

FIGS. 2 and 3 show structural views of a conventional optical fiber characteristics measuring apparatus. The same elements as those in FIG. 1 are denoted by the same symbols and numerals and will not be described further in detail. In FIGS. 2, and 3, a light source unit 10 has a tunable light source 11 and a pulse generator 12 and outputs pulse light with angular frequencies of $\omega_1$, $\omega_2$. The tunable light source 11 is a continuous light output unit. It variably controls the angular frequencies $\omega_1$, $\omega_2$ and outputs continuous light having the desired angular frequencies $\omega_1$, $\omega_2$. The pulse generator 12 converts the continuous light from the tunable light source 11 to pulse light having a desired pulse width and then outputs the pulse light.

A polarization controller 20 arbitrarily polarizes each pulse light from the light source unit 10 in a variable manner (into at least two different polarization states) and outputs the polarized light. A directional coupler 30 outputs the pulse light polarized by the polarization controller 20 to the optical fiber 100, and return light from the optical fiber 100, that is, back scattered light, is inputted to the directional coupler 30. A photodetector 40 detects the light intensity of the back scattered light from the directional coupler 30 in the polarization states of at least four directions synchronously with the pulse light outputted from the light source unit 10, and finds a normalized Stokes vector for each of the angular frequencies $\omega_1$, $\omega_2$.

An arithmetic operation unit 50 has a matrix calculating unit 51, a polarization dispersion vector calculating unit 52, a linear polarization calculating unit 53, and a dispersion value calculating unit 54. The arithmetic operation unit 50 calculates polarization dispersion vectors $\Omega_B$ of the back scattered light on the basis of the Stokes vectors found by the photodetector 40, then calculates linear polarization components of the polarization dispersion vector $\Omega$ in a single direction by using the polarization dispersion vectors $\Omega_B$, and calculates polarization mode dispersion.

The matrix calculating unit 51 calculates a Mueller matrix from the normalized Stokes vector for each of the angular frequencies $\omega_1$, $\omega_2$. The polarization dispersion vector calculating unit 52 calculates the polarization dispersion vectors $\Omega_B$ of the back scattered light at the angular frequencies from the Mueller matrix calculated by the matrix calculating unit 51. The linear polarization calculating unit 53 calculates the magnitude of linear polarization components ($\Omega_1$, $\Omega_2$) of the polarization dispersion vector $\Omega$ in a single direction from the polarization dispersion vectors $\Omega_B$ of the back scattered light calculated by the polarization dispersion vector calculating unit 52. The dispersion value calculating unit 53 calculates a polarization mode dispersion value from the magnitude of the linear polarization components.

A control unit 60 designates the angular frequencies $\omega_1$, $\omega_2$, pulse width and pulse interval to the light source unit 10 and designates the polarization state to the polarization controller 20. The control unit 60 also designates the polarization state to be detected to the photodetector 40 and synchronizes the detection with the pulse light, and designates the calculation to the arithmetic operation unit 50.

The operation of this apparatus will now be described.

The control unit 60 causes the tunable light source 11 to output continuous light at the angular frequency $\omega_1$ and causes the pulse generator 12 to output pulse light with a desired pulse width at a desired pulse interval. Moreover, the control unit 60 causes the polarization controller 20 to output the pulse light with a polarization state of, for example, 0°, to the subject optical fiber 100 via the directional coupler 30.

Then, back scattered light, which is return light from the subject optical fiber 100, is inputted to the photodetector 40 via the directional coupler 30. The photodetector 40 detects the light intensity in four directions (for example, 0°, 45°, 90°, and circular polarization) in accordance with the designation from the control unit 60.

Similarly, the light intensities in four directions are detected with respect to the light at the angular frequency $\omega_1$ and in the polarization state of 45°, the light at the angular, frequency $\omega_2$ and in the polarization state of 0°, and the light at the angular frequency $\omega_2$ and in the polarization state of 45° in accordance with the designation from the control unit 60. The photodetector 40 then calculates a Stokes vector $S_B$ for each of the angular frequencies $\omega_1$, $\omega_2$.

As the Stokes vector $S_B$ is calculated, the control unit 60 instructs the arithmetic operation unit 50 to calculate polarization mode dispersion. In accordance with this instruction, the arithmetic operation unit 50 reads out the Stokes vector $S_B$ from the photodetector 40 and the matrix calculating unit 51 calculates a Mueller matrix $R_B$ of the back scattered light from the Stokes vector $S_B$.

The polarization dispersion vector calculating unit 52 calculates polarization dispersion vectors $\Omega_B$ of the back scattered light from the Mueller matrix $R_B$. That is, when the light intensity of the back scattered light from the subject optical fiber 100 is measured, the relation of the following equation (2) based on the Mueller matrix $R_B$ and Stokes vector $S_B$ holds, similarly to the equation (1).

$$\frac{d\hat{S}_B}{d\omega} = \frac{dR_B}{d\omega} R_B^{-1} \hat{S}_B \tag{2}$$

$\hat{S}_B$ represents Stokes vector $S_B$ of back scattered light, and $R_B$ represents Mueller matrix $R_B$ of back scattered light.

As the polarization dispersion matrix $\Omega_B$ representing the polarization dispersion vectors $\Omega_B$ of the back scattered light, the following equation (3) can be acquired from the equations (1) and (2).

$$\hat{\Omega}_B = \frac{dR_B}{d\omega} R_B^{-1} \quad (3)$$

$\hat{\Omega}_B$ represents polarization dispersion vectors $\Omega_B$.

In this manner, the polarization dispersion vector calculating unit 52 calculates the polarization dispersion vectors $\Omega_B$.

Moreover, the linear polarization calculating unit 53 calculates the magnitude of linear polarization components of the polarization dispersion vector $\Omega$ in a single direction. That is, it is generally known that the relation between the Mueller matrix $R$ and the Mueller matrix $R_B$ of the back scattered light is expressed by the following equation (4) using a matrix M.

$$R_B = MR^T MR \quad (4)$$
$$\left( M = \begin{pmatrix} 1 & 0 & 0 \\ 0 & 1 & 0 \\ 0 & 0 & -1 \end{pmatrix} \right)$$

Therefore, as the equation (4) is substituted into the equation (3), the polarization dispersion vector $\Omega_B$ of the back scattered light, the Mueller matrix R in the single direction, and the linear polarization component $\Omega_L$ of the polarization dispersion vector $\Omega$ in the single direction are in the relation of the following equation (5)

$$\hat{\Omega}_B = 2MR^T \hat{\Omega}_L \quad (5)$$

$(\hat{\Omega}_L = [\Omega_1 \ \Omega_2 \ 0 \ ]^T)$ $\hat{\Omega}_L$ represents linear polarization component vector $\Omega_L$.

In the case of calculating the magnitude $(\Delta\tau_B)$ of the polarization dispersion vector $\Omega_B$ of the back scattered light, the magnitude of the vector converted by MR (transported matrix) on the right side of the equation (5) is not changed because the matrix M and the Mueller matrix R are orthogonal matrices. Therefore, the following equation holds.

$$\Delta\tau_B = |\hat{\Omega}_B| = 2\sqrt{\Omega_1^2 + \Omega_2^2}$$

In this manner, the linear polarization calculating unit 53 calculates the magnitude of the linear polarization components $(\Omega_1, \Omega_2)$ of the polarization dispersion vector $\Omega$ in the single direction. On the statistical assumption of Gaussian distribution as the distribution of the components $\Omega_1$ to $\Omega_3$ of the polarization dispersion vector $\Omega$, the relation between the magnitude $(\Delta\tau_B)$ of the polarization dispersion vector $\Omega_B$ of the back scattered light and the magnitude $(\Delta\tau)$ of the polarization dispersion vector $\Omega$ of polarization mode dispersion to be found is expressed by the following equation.

$$\langle \Delta\tau \rangle = \langle \Delta\tau_B \rangle \frac{2}{\pi}$$

$\langle \Delta\tau_B \rangle$ is a statistical average value of values that are measured many times under various conditions.

Therefore, the dispersion value calculating unit 54 calculates the value of polarization mode dispersion from the polarization dispersion vector $\Omega_B$ acquired from the back scattered light. (See, for example, Fabrizio Corsi, Andrea Galtarossa, Luca Palmieri, "Polarization Mode Dispersion Characterization of Single-Mode Optical Fiber Using Back-scattering Technique," JOURNAL OF LIGHTWAVE TECHNOLOGY (U.S.), Laser & Electro-Optics Society (LEOS), October 1998, Vol. 16, No. 10, pp. 1832–1843.)

In this manner, the magnitude $(\Delta\tau_B)$ of the polarization dispersion vector $\Omega_B$ of pulse light of two wavelengths (angular frequencies $\omega_1, \omega_2$) is calculated and polarization mode dispersion $(\Delta\tau)$ is measured.

However, the apparatus shown in FIGS. 2 and 3 has a problem that it cannot detect the circular polarization component of birefringence within the subject optical fiber 100 simply and directly, as described in J. N. Ross, "Birefringence measurement in optical fibers by polarization-optical time-domain reflectometry," Applied Optics (U.S.), Optical Society of America (OSA), October 1982, Vol. 21, No. 19, pp. 3489–3495. As is clear from the equation (5), only the effect of the linear polarization components $(\Omega_1, \Omega_2)$ is left and the effect of the circular polarization component $\Omega_3$ is eliminated. Therefore, when the magnitude $(\Delta\tau_B)$ of the polarization dispersion vector $\Omega_B$ of the back scattered light is compared with the polarization mode dispersion $(\Delta\tau)$, the following formula holds.

$$\Delta\tau_B = 2\sqrt{\Omega_1^2 + \Omega_2^2} < 2\sqrt{\Omega_1^2 + \Omega_2^2 + \Omega_3^2} = 2\Delta\tau$$

Of course, the polarization dispersion vector $\Omega_B$ acquired from the back scattered light only includes the linear polarization components $(\Omega_1, \Omega_2)$ of the polarization dispersion vector $\Omega$ in the single direction. The OTDR technique measures the light entered and returning from the subject optical fiber 100. If $\Delta\tau = \Delta\tau_B/2$ is simply assumed, polarization mode dispersion $\Delta\tau$ cannot be calculated accurately. For example, if the circular polarization component $\Omega_3$ increases because of torsion of the subject optical fiber 100 or the like, there is a possibility that polarization mode dispersion $(\Delta\tau)$ takes a relatively small value.

Generally, the average magnitude $\langle \Delta\tau_B \rangle$ of the polarization dispersion vectors acquired from the back scattered light is multiplied by 0.64 (which is approximately $2/\pi$), as shown in the above-described equation. However, since this value is acquired from many numerical simulations and statistics, the value is not effective for all the subject optical fibers 100 and it is difficult to accurately find polarization mode dispersion, that is, the characteristics of the optical fibers

SUMMARY OF THE INVENTION

It is an object of this invention to realize an apparatus and method for measuring characteristics of optical fibers that enable accurate measurement of characteristics of subject optical fibers.

DETAILED DESCRIPTION OF THE PREFERRED EMBODIMENTS

Embodiments of this invention will now be described with reference to the drawings.

[First Embodiment]

Figure 1:
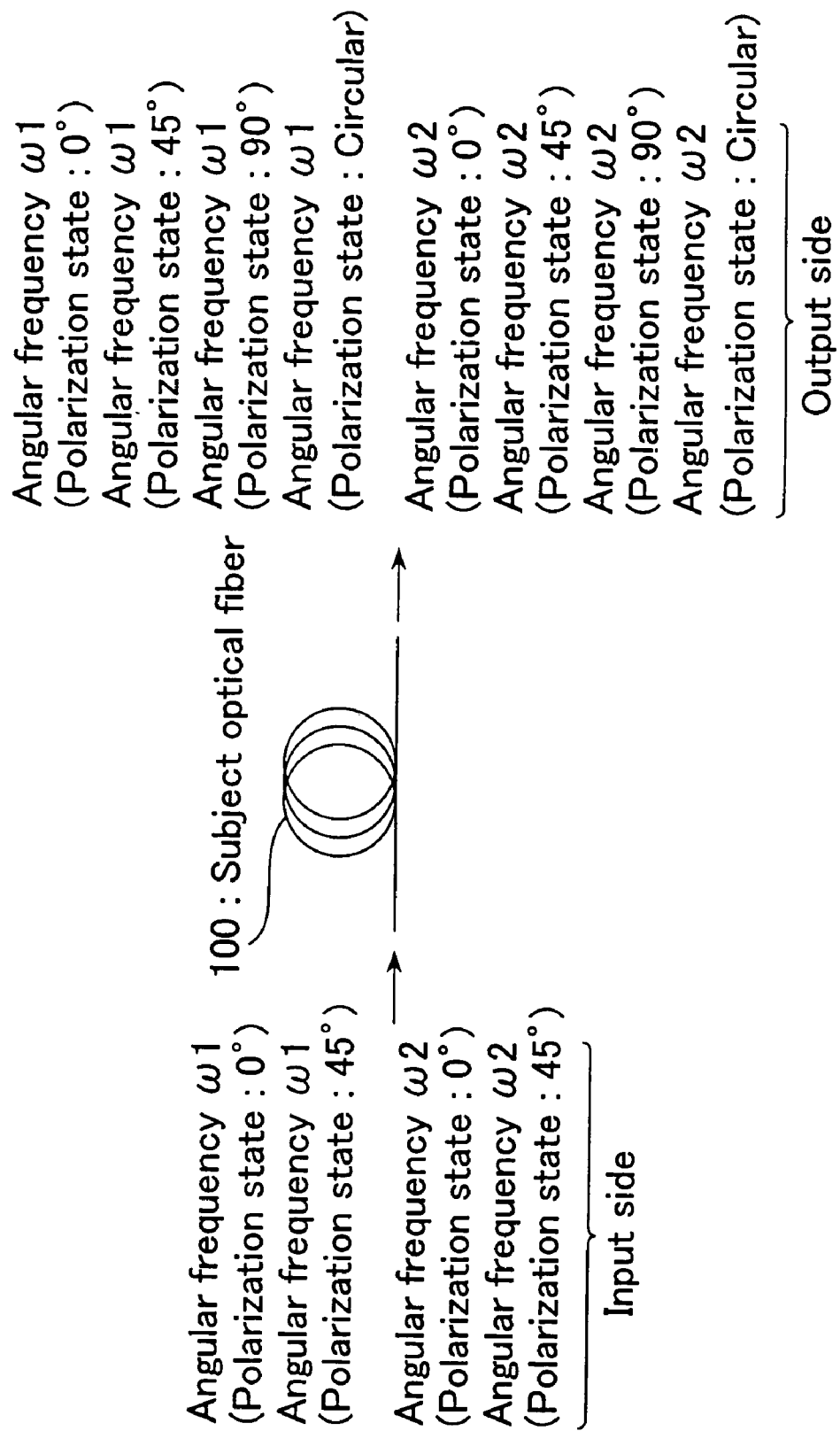
FIG. 1 is a view showing a first structure of a conventional optical fiber characteristics measuring apparatus.
Figure 2:
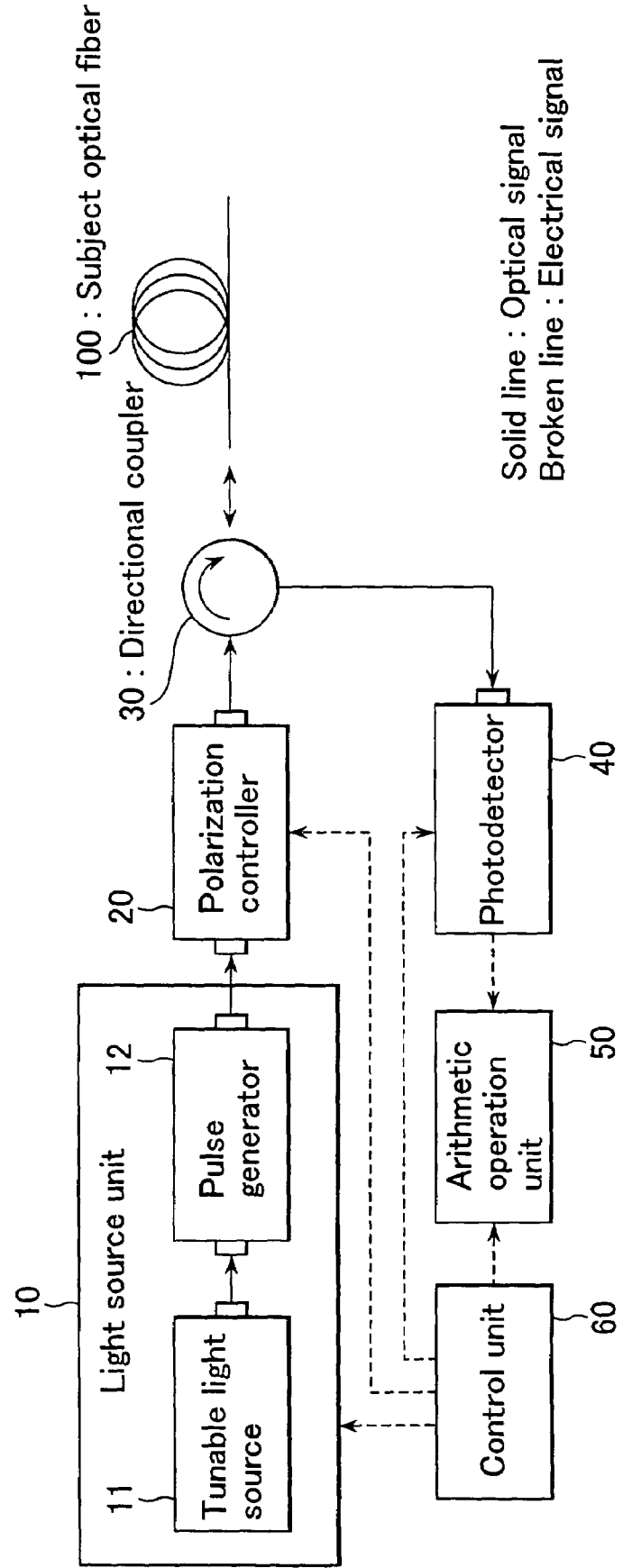
FIG. 2 is a view showing a second structure of a conventional optical fiber characteristics measuring apparatus.
Figure 3:
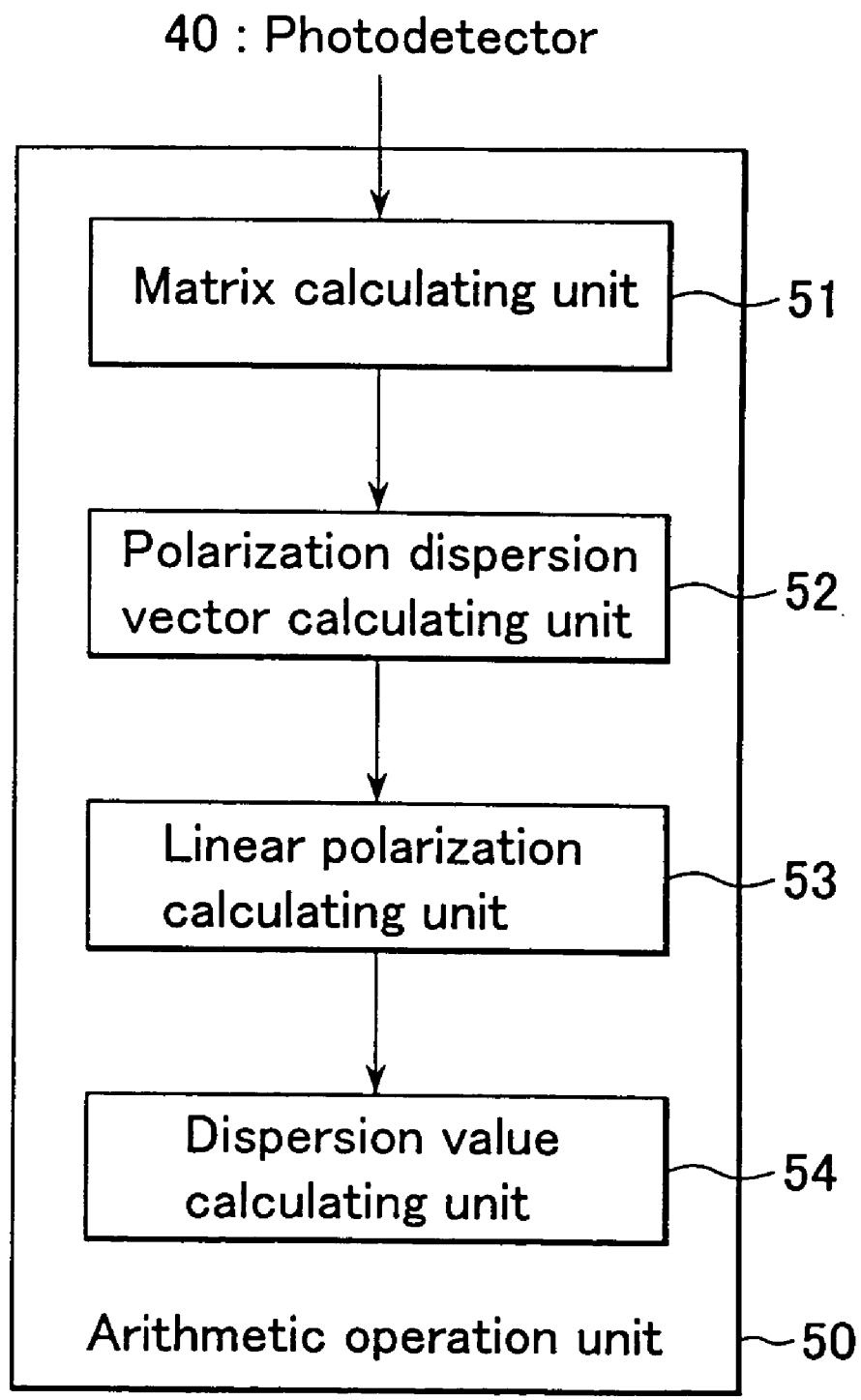
FIG. 3 is a view showing the structure of an arithmetic operation unit 50 in the apparatus shown in FIG. 2.
Figure 4:
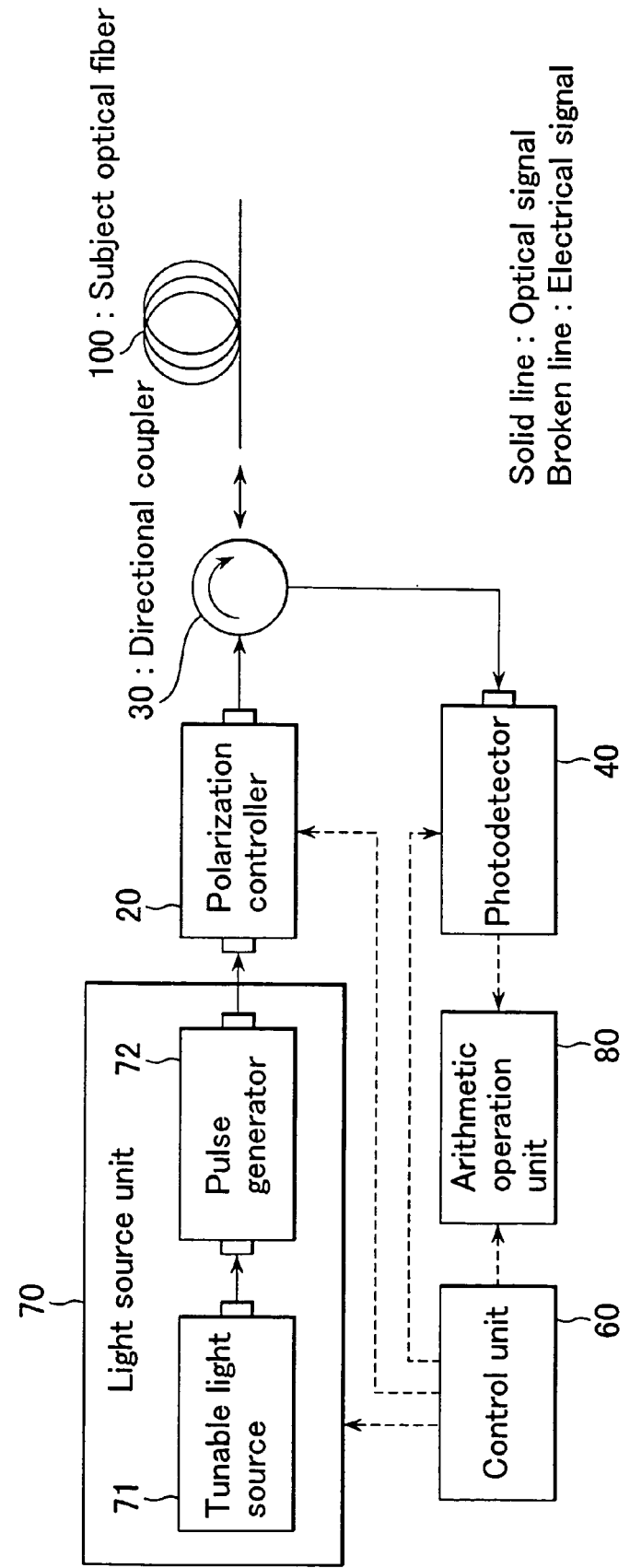
FIG. 4 is a structural view showing a first embodiment of this invention.
Figure 5:
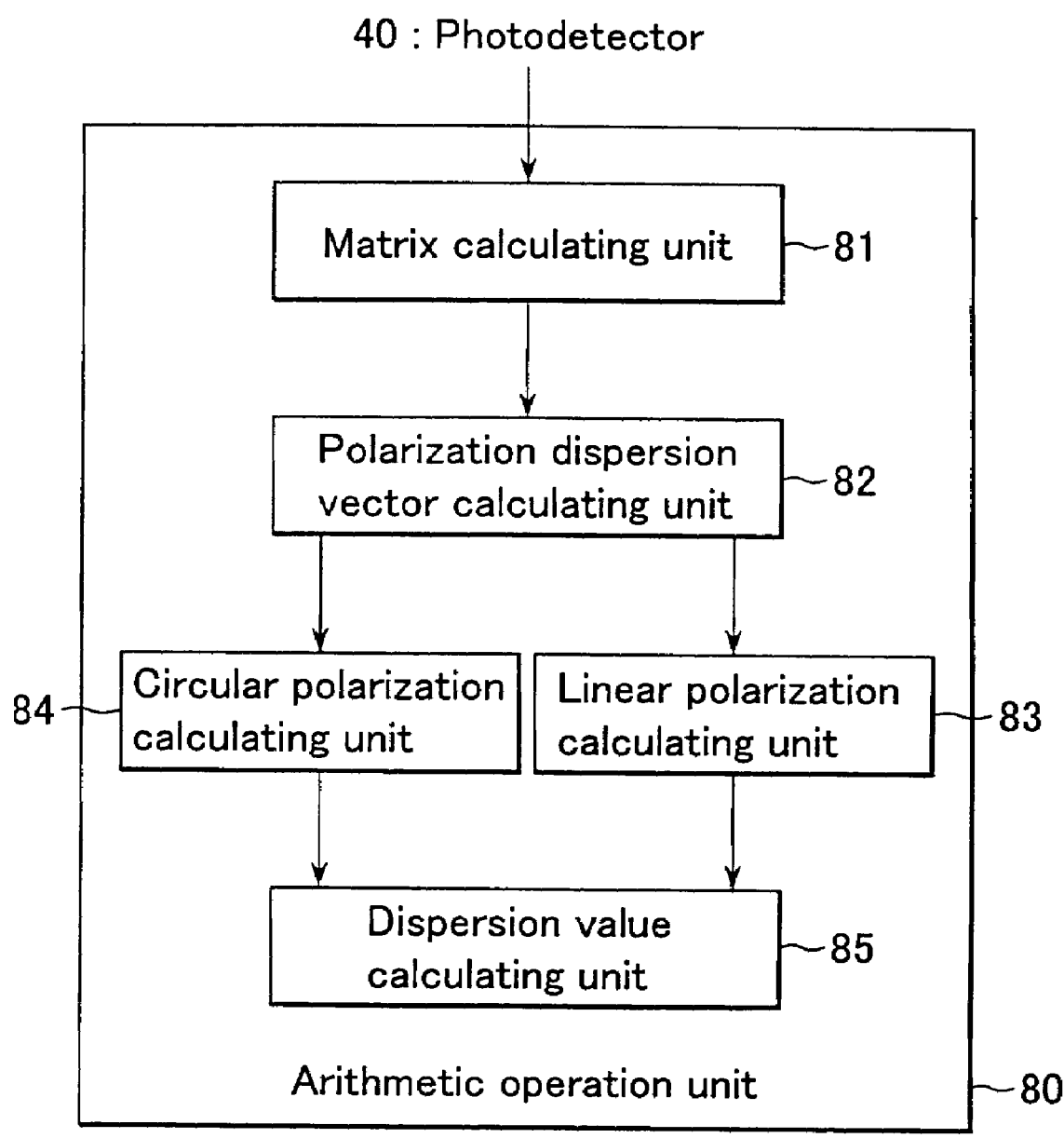
FIG. 5 is a view showing the structure of an arithmetic operation unit 80 in the apparatus shown in FIG. 4.

FIGS. 4 and 5 are structural views showing a first embodiment of this invention. The same elements as those shown in FIGS. 2 and 3 are denoted by the same numerals and will not be described further in detail. In FIG. 4, a light source unit 70 is provided instead of the light source unit 10. An arithmetic operation unit 80 is provided instead of the arithmetic operation unit 50.

The light source unit 70 has a tunable light source 71 and a pulse generator 72, and outputs at least three kinds of pulse light having different angular frequencies, for example, three kinds of pulse light having angular frequencies $\omega_1$, $\omega_2$, $\omega_3$ (the angular frequencies $\omega_1$, $\omega_2$, $\omega_3$ are slightly different from each other at an angular frequency spacing $\Delta\omega$). The tunable light source 71 is a continuous light output unit. It variably controls the angular frequencies $\omega_1$, $\omega_2$, $\omega_3$ and outputs continuous light having the desired angular frequencies $\omega_1$, $\omega_2$, $\omega_3$. The pulse generator 72 converts the continuous light from the tunable light source 71 to pulse light having a desired pulse width and outputs the pulse light to the polarization controller 20.

In FIG. 5, the arithmetic operation unit 80 has a matrix calculating unit 81, a polarization dispersion vector calculating unit 82, a linear polarization calculating unit 83, a circular polarization calculating unit 84, and a dispersion value calculating unit 85. The arithmetic operation unit 80 calculates polarization dispersion vectors $\Omega_B$ of back scattered light on the basis of a Stokes vector found by the photodetector 40, then calculates the magnitude of linear polarization components and the magnitude of a circular polarization component of a polarization dispersion vector $\Omega$ in a single direction by using the polarization dispersion vectors $\Omega_B$, and calculates polarization mode dispersion from these magnitudes.

The matrix calculating unit 81 calculates a Mueller matrix from the normalized Stokes vector for each of the angular frequencies $\omega_1$, $\omega_2$, $\omega_3$. The polarization dispersion vector calculating unit 82 calculates the polarization dispersion vectors $\Omega_B$ of the back scattered light in accordance with the angular frequency from the Mueller matrix calculated by the matrix calculating unit 81. The linear polarization calculating unit 83 calculates the magnitude of the linear polarization components ($\Omega_1$, $\Omega_2$) of the polarization dispersion vector $\Omega$ in a single direction from the polarization dispersion vectors $\Omega_B$ of the back scattered light calculated by the polarization dispersion vector calculating unit 82. The circular polarization calculating unit 84 calculates the magnitude of the circular polarization component ($\Omega_3$) of the polarization dispersion vector $\Omega$ in the single direction from the difference between the polarization dispersion vectors $\Omega_B$ of the back scattered light calculated by the polarization dispersion vector calculating unit 82. The dispersion value calculating unit 85 calculates the value of polarization mode dispersion from the magnitude of the circular polarization component calculated by the circular polarization calculating unit 84 and the magnitude of the linear polarization components calculated by the linear polarization calculating unit 83.

The operation of this apparatus will now be described.

Figure 6:
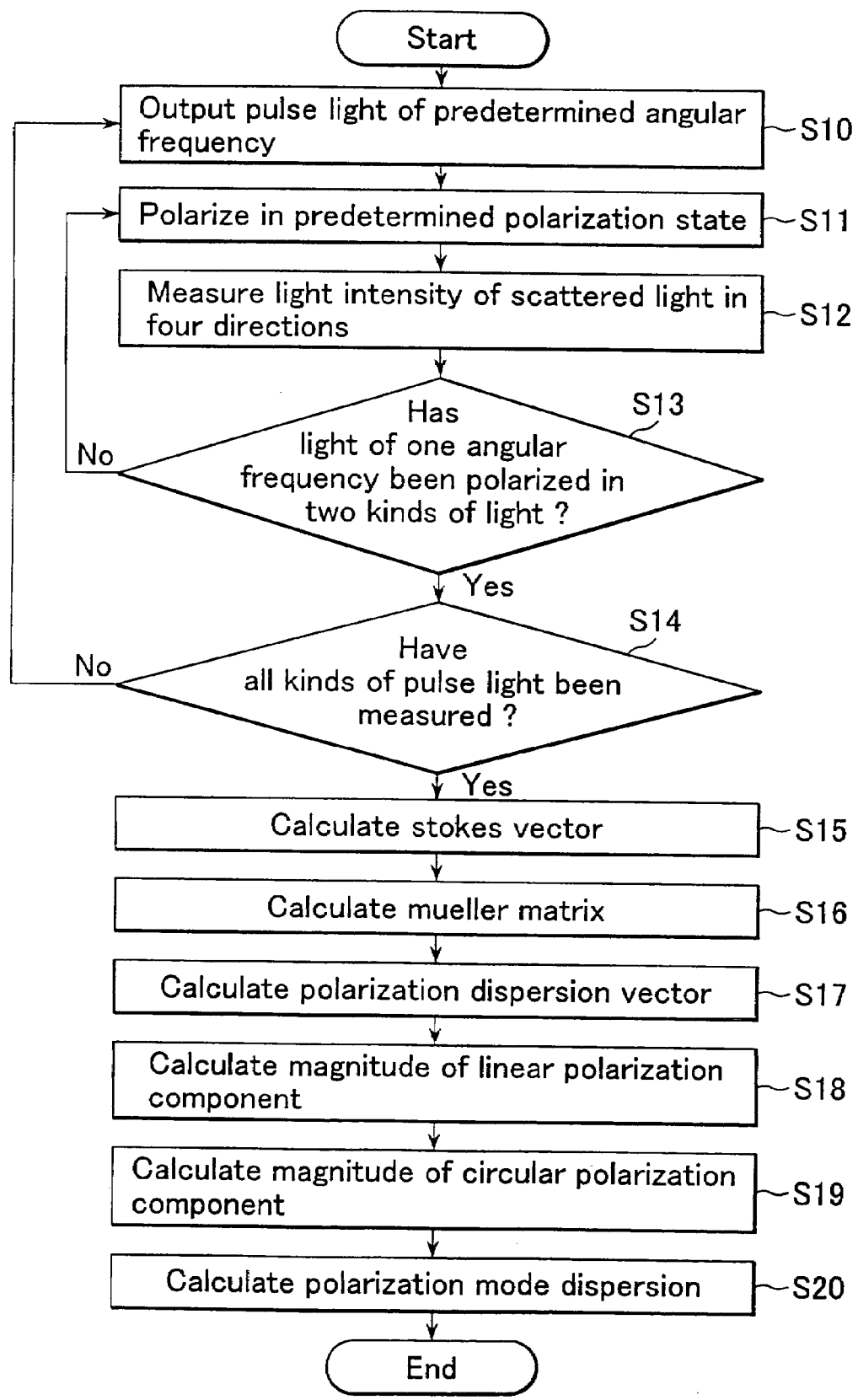
FIG. 6 is a flowchart showing the operation of the apparatus shown in FIG. 4.

FIG. 6 is a flowchart showing the operation of the apparatus shown in FIGS. 4 and 5.

The control unit 60 causes the tunable light source 71 of the light source unit 70 to output continuous light at the angular frequency $\omega_1$ and causes the pulse generator 72 to output pulse light with a desired pulse width and at a desired pulse interval (S10). The control unit 60 also causes the polarization controller 20 to output the pulse light with a polarization state of, for example, 0°, to the subject optical fiber 100 via the directional coupler 30 (S11).

Then, back scattered light, which is return light from the subject optical fiber 100, is inputted to the photodetector 40 via the directional coupler 30. The photodetector 40 detects the light intensity in four directions (for example, 0°, 45°, 90°, and circular polarization) synchronously with the pulse light from the light source unit 70 in accordance with the designation from the control unit 60. The back scattered light is split into polarization states in four directions by a combination of a polarization device, a phase device such as a ½ wavelength plate and a ¼ wavelength plate, and a light receiving device, and the light intensities are detected (S12).

In the case where one polarization state of 0° is measured at one angular frequency $\omega_1$, the control unit 60 causes the polarization controller 20 to change the polarization state of the pulse light to, for example, 45°, and to output the pulse light to the subject optical fiber 100 via the directional coupler 30, and then the control unit 60 causes the photodetector to detect the light intensity (S13, S11, S12).

In the case where detection in the different polarization states of 0° and 45° at one angular frequency $\omega_1$ is completed, the control unit 60 similarly causes the photodetector to detect and measure the light intensity at the angular frequencies $\omega_2$ and $\omega_3$, at which the light intensity has not been detected yet (S14, S11 to S13). In short, six kinds of pulse light are inputted to the subject optical fiber 100, that is, light in the polarization states of 0° and 45° at the angular frequency $\omega_1$, light in the polarization states of 0° and 45 at the angular frequency $\omega_2$, and light in the polarization states of 0° and 45° at the angular frequency $\omega_3$.

When detection of the light intensity at all the angular frequencies $\omega_1$ to $\omega_3$ is completed, a Stokes vector $S_B$ is found for each of the angular frequencies $\omega_1$, $\omega_2$, $\omega_3$ (S14, S15).

As the Stokes vector $S_B$ is found, the control unit 60 instructs the arithmetic operation unit 80 to calculate polarization mode dispersion. In accordance with this instruction, the arithmetic operation unit 80 reads out the Stokes vector $S_B$ from the photodetector 40 and the matrix calculating unit 81 calculates a Mueller matrix $R_B$ of the back scattered light from the Stokes vector $S_B$, similarly to the matrix calculating unit 51 (S16). While the matrix calculating unit 81 find each Mueller matrix $R_B$ after the photodetector 40 finds all the Stokes vectors $S_B$ for the angular frequencies $\omega_1$, $\omega_2$, $\omega_3$, the matrix calculating unit 81 may calculate the Mueller matrix $R_B$ every time the Stokes vector $S_B$ for each of the angular frequencies $\omega_1$, $\omega_2$, $\omega_3$ is found.

Then, the polarization dispersion vector calculating unit 82 calculates the polarization dispersion vectors $\Omega_B$ of the back scattered light in accordance with the angular frequencies $\omega_1$, $\omega_2$, $\omega_3$ from the Mueller matrix $R_B$, similarly to the polarization dispersion vector calculating unit 52. For example, the polarization dispersion vectors $\Omega_B$ are calculated using a combination of $\omega_1$, $\omega_2$ and a combination of $\omega_2$, $\omega_3$ (S17). Moreover, the linear polarization calculating unit 83 calculates the magnitude of linear polarization components ($\Omega_1$, $\Omega_2$) of the polarization dispersion vector $\Omega$ in the single direction, similarly to the linear polarization calculating unit 53 (S18).

Then, the circular polarization calculating unit 84 calculates the magnitude of a circular polarization component $\Omega_3$ of the polarization dispersion vector $\Omega$ in the single direction from the difference between the polarization dispersion vectors $\Omega_B$ of the back scattered light calculated by the polarization dispersion vector calculating unit 82. That is, the polarization dispersion vector $\Omega_B$ of the back scattered light acquired by general measurement in a single direction using OTDR is expressed by the equation (5) as described above, and this equation (5) can be differentiated as in the following equation.

$$\frac{d\hat{\Omega}_B}{d\omega} = 2M\left(\frac{dR^T}{d\omega}\hat{\Omega}_L + R^T\frac{d\hat{\Omega}_L}{d\omega}\right)$$

In the above-described equation, it can be assumed that the polarization dispersion vector $\Omega$ or linear polarization component vector $\Omega_L$ in a single direction is constant with respect to the very small interval of $\omega$. Therefore, the following equation holds.

$$\frac{d\hat{\Omega}_L}{d\omega} = 0$$

Therefore, the following equation (6) is acquired.

$$\frac{d\hat{\Omega}_B}{d\omega} = 2M\frac{dR^T}{d\omega}\hat{\Omega}_L \quad (6)$$

Meanwhile, since the polarization dispersion matrix $\Omega$ representing the polarization dispersion vector $\Omega$ and the Mueller matrix R are expressed by the equation (1) and the Mueller matrix R is an orthogonal matrix, the following equation holds.

$$\Omega = \frac{dR}{d\omega}R^{-1} = \frac{dR}{d\omega}R^T$$

Since the polarization dispersion matrix $\Omega$ is an antisymmetric matrix, the following equation holds.

$$\Omega^T = -\Omega = R\frac{dR^T}{d\omega}$$

Therefore, it can be expressed as follows.

$$\frac{dR^T}{d\omega} = -R^T\Omega$$

Therefore, the equation (6) can be expressed as follows, using the circular polarization component vector $\Omega_C$ of the polarization dispersion vector $\Omega$.

$$\frac{d\hat{\Omega}_B}{d\omega} = -2MR^T(\hat{\Omega}_L + \hat{\Omega}_C) \times \hat{\Omega}_L$$
$$= -2MR^T\hat{\Omega}_C \times \hat{\Omega}_L$$
$$= -2\Omega_3 MR^T\hat{\Omega}_{L\perp}$$

$\hat{\Omega}_C$ represents circular polarization component vector $\Omega_C$.

In this case, this equation holds.

$$\hat{\Omega}_{L\perp} = \begin{pmatrix} -\Omega_2 \\ \Omega_1 \\ 0 \end{pmatrix}$$

Therefore, in consideration of the equation (5), the following equation definitely holds.

$$|\hat{\Omega}_{L\perp}| = |\hat{\Omega}_L| = |\hat{\Omega}_B|/2$$

From the above-described calculation, the following equation holds using the polarization dispersion vector $\Omega_B$.

$$\left|\frac{d\hat{\Omega}_B}{d\omega}\right| = |\Omega_3||\hat{\Omega}_B|$$

That is, the magnitude $|\Omega_3|$ of the circular polarization component is expressed by the following equation (7).

$$|\Omega_3| = \left|\frac{d\hat{\Omega}_B}{d\omega}\right| / |\hat{\Omega}_B| \quad (7)$$

In this manner, the circular polarization calculating unit 84 further differentiates the polarization dispersion vector $\Omega_B$ calculated by the polarization dispersion vector calculating unit 82 and divides the magnitude of the differentiated vector by the magnitude of the polarization dispersion vector $\Omega_B$, thereby calculating the magnitude of the circular polarization component of polarization mode dispersion (S19). Then, the dispersion value calculating unit 85 calculates the value of polarization mode dispersion ($\Delta\tau$) from the magnitude of the circular polarization component calculated by the circular polarization calculating unit 84 and the magnitude of the linear polarization components calculated by the linear polarization calculating unit 83 (S20) Moreover, polarization mode dispersion may be found at each position in the longitudinal direction of the subject optical fiber 100 and the distribution of polarization mode dispersion in the longitudinal direction of the subject optical fiber 100 may be found.

In this manner, the photodetector 40 detects the back scattered light of each pulse light at the angular frequencies $\omega_1$ to $\omega_3$ outputted from the light source unit 70, separately in the polarization states in at least four directions, and thus find the normalized Stokes vector. Then, the arithmetic operation unit 80 calculates the magnitude of the linear polarization components and the magnitude of the circular polarization component of the polarization dispersion vector Ω on the basis of the Stokes vector. Therefore, it is not necessary to use the results of numerical simulations and statistics for the calculation of polarization mode dispersion. This enables accurate measurement of polarization mode dispersion.

[Second Embodiment]

Figure 7:
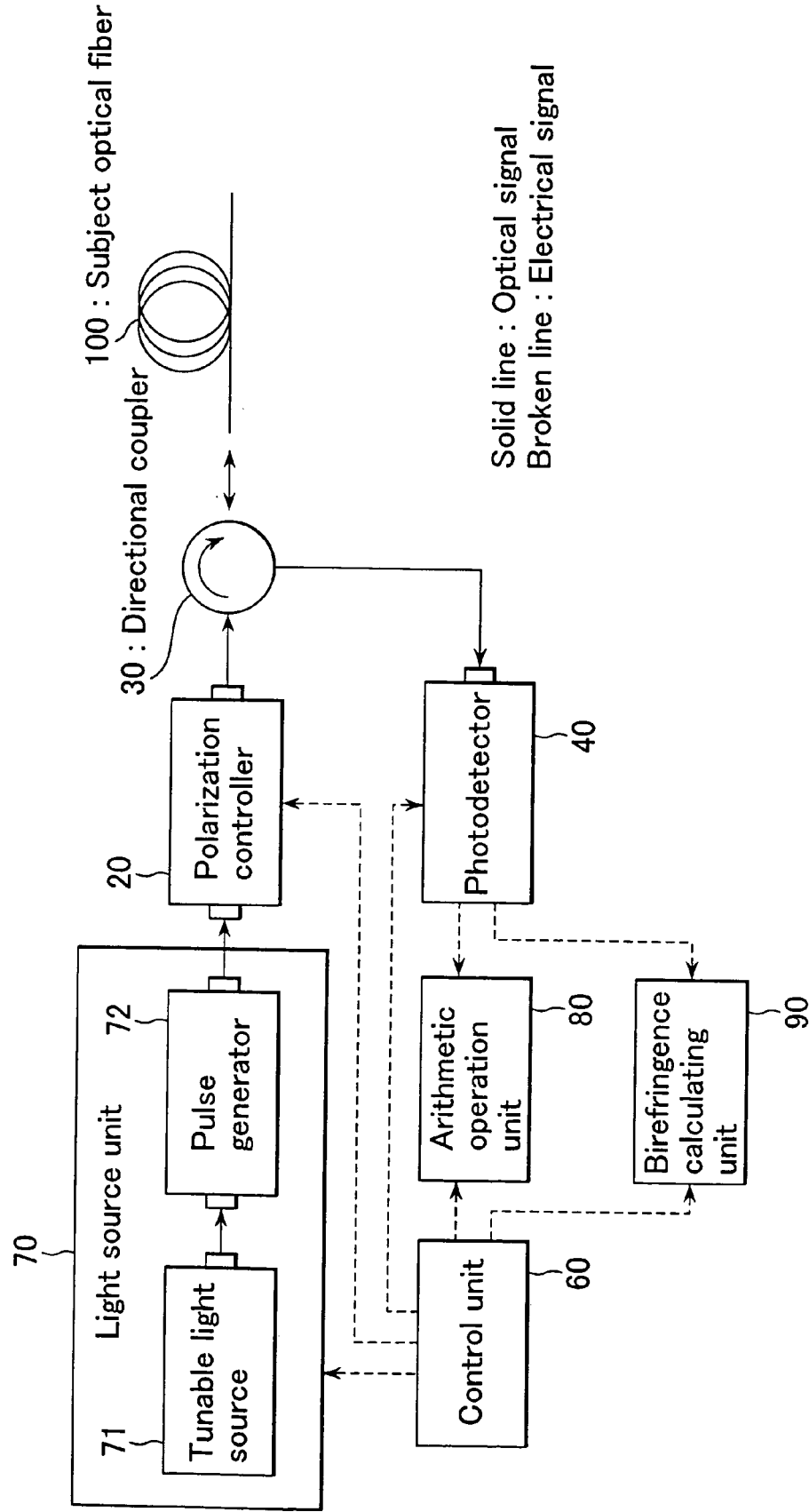
FIG. 7 is a structural view showing a second embodiment of this invention.

The embodiment of measuring polarization mode dispersion by the apparatus shown in FIGS. 4 and 5 is described above. Polarization mode dispersion is generated by birefringence in the optical fiber. That is, it is also important to measure the magnitude of birefringence, which is one of the characteristics in the longitudinal direction of the subject optical fiber 100. FIG. 7 is a structural view showing a second embodiment of this invention. In FIG. 7, the same elements as those shown in FIG. 4 are denoted by the same numerals and will not be described further in detail.

In FIG. 7, a birefringence calculating unit 90 is further provided. As the photodetector 40 detects the light intensity at least at three positions z1, z2, z3 (z1, z2, z3 are slightly different from each other at a very small position spacing Δz) in the longitudinal direction of the subject optical fiber 100, the birefringence calculating unit 90 calculates a birefringence vector of back scattered light on the basis of a normalized Stokes vector found for each of the positions, then calculates the magnitude of linear polarization components and the magnitude of a circular polarization component of the birefringence vector, and calculates the magnitude of birefringence in the longitudinal direction of the subject optical fiber 100 from these magnitudes.

Figure 8:
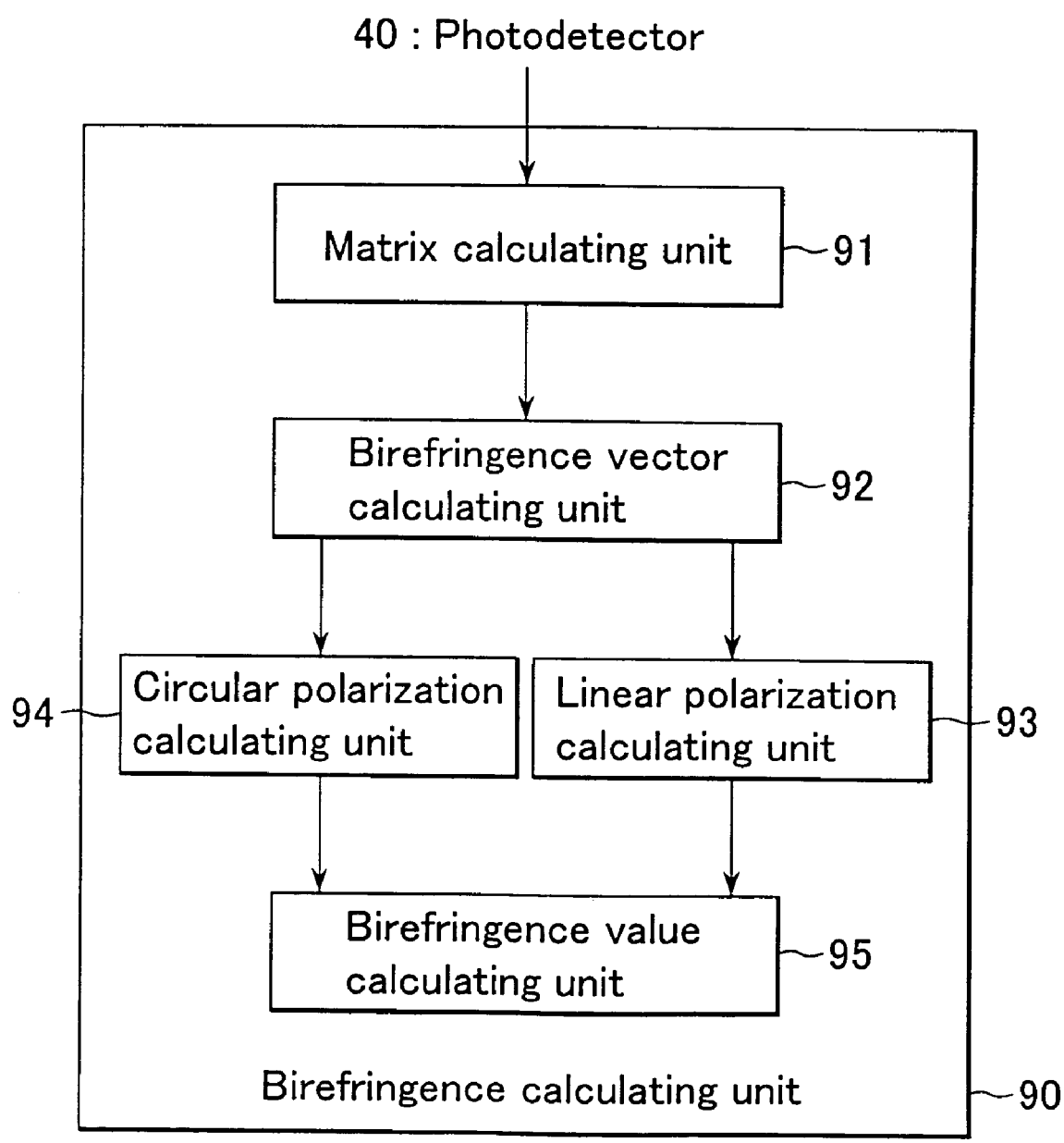
FIG. 8 is a view showing the structure of a birefringence calculating unit 90 in the apparatus shown in FIG. 7.

FIG. 8 shows a structural view of the birefringence calculating unit 90. In FIG. 8, the birefringence calculating unit 90 has a matrix calculating unit 91, a birefringence vector calculating unit 92, a linear polarization calculating unit 93, a circular polarization calculating unit 94, and a birefringence value calculating unit 95.

The matrix calculating unit 91 calculates a Mueller matrix from the normalized Stokes vector found for each position. The birefringence vector calculating unit 92 calculates birefringence vectors of the back scattered light in accordance with the position from the Mueller matrix calculated by the matrix calculating unit 91. The linear polarization calculating unit 93 calculates the magnitude of linear polarization components of a birefringence vector in a single direction from the birefringence vectors of the back scattered light calculated by the birefringence vector calculating unit 92. The circular polarization calculating unit 94 calculates the magnitude of a circular polarization component of the birefringence vector in the single direction from the difference between the birefringence vectors of the back scattered light calculated by the birefringence vector calculating unit 92. The birefringence value calculating unit 95 calculates the magnitude of birefringence in the single direction from the magnitude of the circular polarization component calculated by the circular polarization calculating unit 94 and the magnitude of the linear polarization components calculated by the linear polarization calculating unit 93.

The operation of this apparatus will now be described.

The photodetector 40 detects the light intensity of back scattered light of pulse light (for example, at an angular frequency $\omega_1$, of angular frequencies $\omega_1$ to $\omega_3$) from the light source unit 70 in polarization states of at least four directions (for example, 0°, 45°, 90°, and circular polarization) synchronously with this pulse light in accordance with the designation from the control unit 60. The light intensity of back scattered light from at least three different positions z1, z2, z3 in the longitudinal direction of the subject optical fiber 100 is detected. Then, normalized Stokes vectors at the positions z1 to z3 are found.

The control unit 60 instructs the birefringence calculating unit 90 to calculate birefringence. In accordance with this instruction, the birefringence calculating unit 90 reads out a Stokes vector $S_B$ from the photodetector 40, and the matrix calculating unit 91 calculates a Mueller matrix $R_B$ of the back scattered light from the Stokes vector $S_B$. The birefringence vector calculating unit 92 calculates birefringence vectors $\beta_B$ of the back scattered light from the Mueller matrix $R_B$. That is, if a change of the Stokes vector S is considered to be a change in the longitudinal direction of the subject optical fiber 100, it can be expressed by the following equation (8). Therefore, the birefringence vectors $\beta_B$ are calculated as in the case of the polarization dispersion vectors $\Omega_B$.

$$\frac{d\hat{S}}{dz} = \frac{dR}{dz}\hat{S}_0 = \frac{dR}{dz}R^{-1}R\hat{S}_0 = \frac{dR}{dz}R^{-1}\hat{S} = \hat{\beta} \times \hat{S} \qquad (8)$$

$\hat{\beta}$ represents birefringence vector $\beta$

The linear polarization calculating unit 93 calculates the magnitude of linear polarization components of the birefringence vector β in a single direction from the birefringence vectors $\beta_B$ of the back scattered light calculated by the birefringence vector calculating unit 92. That is, the birefringence vector β in the equation (8) expresses local birefringence in the polarization state space. Therefore, as is clear from the comparison of the equations (1) and (8), the birefringence vector β can be handled similarly to the polarization dispersion vector Ω. As described in, for example, Fabrizio Corsi, Andrea Galtarossa, Luca Palmieri, "Beat Length Characterization Based on Backscattering Analysis in Randomly Perturbed Single-Mode Fibers," JOURNAL OF LIGHTWAVE TECHNOLOGY (U.S.), Laser & Electro-Optics Society (LEOS), July 1999, Vol. 17, No. 7, pp. 1172–1178, the birefringence vector $\beta_B$ acquired from the back scattered light and the linear polarization component vector $\beta_L$ of the birefringence vector β in the single direction are expressed by the following equation, similarly to the equation (5).

$$\hat{\beta}_B = 2MR^T \hat{\beta}_L$$

$$(\hat{\beta}_L = [\beta_1 \ \beta_2 \ 0]^T)$$

$\hat{\beta}_B$ represents birefringence vector $\beta_B$ acquired from back scattered light, and $\hat{\beta}_L$ represents linear polarization component vector $\beta_L$ of birefringence vector $\hat{\beta}$.

In this manner, the linear polarization calculating unit 93 calculates the magnitude of the linear polarization components ($\beta_1$, $\beta_2$) of the birefringence vector β in the single direction. Of course, as in the case of the polarization dispersion vector $\Omega_B$, the effect of the circular polarization component $\beta_3$ has been eliminated. Thus, the circular polarization calculating unit 94 calculates the magnitude of the circular polarization component of the birefringence vector β in the single direction from the birefringence vectors $\beta_B$ of the back scattered light calculated by the birefringence vector calculating unit 92. That is, as in the calculation of the equation (7) for the polarization dispersion vector $\Omega_B$, the magnitude of the circular polarization component can be expressed by the following equation (9).

$$|\beta_3| = \left|\frac{d\hat{\beta}_B}{dz}\right| / |\hat{\beta}_B| \qquad (9)$$

The operation up to the detection of the pulse light from the light source unit 70 by the photodetector 40 and the operation of the arithmetic operation unit 80 are similar to the operations in the apparatus shown in FIG. 4 and therefore will not be described further in detail.

As described above, the circular polarization calculating unit 94 further differentiates the birefringence vector $\beta_B$ calculated by the birefringence vector calculating unit 92 and divides the differentiated magnitude by the magnitude of the birefringence vector $\beta_B$, thereby calculating the magnitude of the circular polarization component of birefringence. Then, the birefringence value calculating unit 95 calculates birefringence from the magnitude of the circular polarization component calculated by the circular polarization calculating unit 94 and the magnitude of the linear polarization components calculated by the linear polarization calculating unit 93. Birefringence at a desired position may be found from the light intensity at three points (z1, z2, z3) around the desired position in the longitudinal direction of the subject optical fiber 100, and then distribution of birefringence in the longitudinal direction of the subject optical fiber 100 may be found.

In this manner, the back scattered light from the different positions z1, z2, z3, of the pulse light having the angular frequency $\omega_1$ outputted from the light source unit 70, is split into polarization states of at least four directions and thus detected by the photodetector 40, and the normalized Stokes vectors are found. Then, the arithmetic operation unit 90 calculates the magnitude of the linear polarization components and the magnitude of the circular polarization component of the birefringence vector β on the basis of the Stokes vectors. Therefore, it is not necessary to use the results of numerical simulations and statistics for the calculation of birefringence. This enables accurate measurement of birefringence.

This invention is not limited to these embodiments and the following structures may be employed.

While the arithmetic operation unit 80 and the birefringence calculating unit 90 are provided in the apparatus shown in FIG. 7, the arithmetic operation unit 80 need not be provided in the case of calculating birefringence alone. In this case, the light source unit 70 may output light at one angular frequency.

Although the tunable light source 71 outputs light while sequentially changing the angular frequencies $\omega_1$ to $\omega_3$ in the apparatuses shown in FIGS. 4 and 7, three tunable light sources 71 may be provided to simultaneously output light at the angular frequencies $\omega_1$ to $\omega_3$. In this case, a multiplexer can be provided between the tunable light sources 71 and the pulse generator 72, and a branching filter can be provided between the directional coupler 30 and the photodetector 40.

While the tunable light source 71 outputs continuous light having different angular frequencies (at least three angular frequencies) in the above-described embodiment, at least three light sources for outputting light having a fixed wavelength may be provided instead of the tunable light source 71.

Moreover, though the polarization controller 20 polarizes pulse light into two kinds of polarization states, it may polarize pulse light into plural kinds of polarization states.

This invention has the following effects.

The photodetector finds a normalized Stokes vector from back scattered light of each pulse light having at least three kinds of different angular frequencies. The arithmetic operation unit calculates the magnitude of linear polarization components and the magnitude of a circular polarization component of a polarization dispersion vector on the basis of the Stokes vector. Therefore, it is not necessary to use the results of numerical simulations and statistics for the calculation of polarization mode dispersion. This enables accurate measurement of polarization mode dispersion.

The photodetector splits back scattered light of each pulse light having at least three kinds of different angular frequencies outputted from the light source unit into polarization states of at least four directions, detects the split back scattered light, and finds a normalized Stokes vector. The arithmetic operation unit calculates the magnitude of linear polarization components and the magnitude of a circular polarization component of a polarization dispersion vector on the basis of the Stokes vector. Therefore, it is not necessary to use the results of numerical simulations and statistics for the calculation of polarization mode dispersion. This enables accurate measurement of polarization mode dispersion.

The photodetector finds a normalized Stokes vector from back scattered light from each of at least three different positions. The arithmetic operation unit calculates the magnitude of linear polarization components and the magnitude of a circular polarization component of a birefringence vector on the basis of the Stokes vector. Therefore, it is not necessary to use the results of numerical simulations and statistics for the calculation of the magnitude of birefringence. This enables accurate measurement of birefringence.

The photodetector splits back scattered light from each of at least three different positions, of pulse light outputted from the light source unit, into polarization states of at least four directions, detects the split back scattered light, and finds a normalized Stokes vector. The arithmetic operation unit calculates the magnitude of linear polarization components and the magnitude of a circular polarization component of a birefringence vector on the basis of the Stokes vector. Therefore, it is not necessary to use the results of numerical simulations and statistics for the calculation of birefringence. This enables accurate measurement of birefringence.

Back scattered light of each pulse light having at least three different angular frequencies outputted from the light source unit is split into polarization states of at least four directions and thus detected, and a normalized Stokes vector is found. On the basis of the Stokes vector, the magnitude of linear polarization components and the magnitude of a circular polarization component of a polarization dispersion vector are calculated. Therefore, it is not necessary to use the results of numerical simulations and statistics for the calculation of polarization mode dispersion. This enables accurate measurement of polarization mode dispersion.

Back scattered light from each of at least three different positions, of pulse light outputted from the light source unit, is split into polarization states of at least four directions and thus detected, and a normalized Stokes vector is found. On the basis of the Stokes vector, the magnitude of linear polarization components and the magnitude of a circular polarization component of a birefringence vector are calculated. Therefore, it is not necessary to use the results of numerical simulations and statistics for the calculation of birefringence. This enables accurate measurement of birefringence.

What is claimed is:

1. An optical fiber characteristics measuring apparatus in which pulse light is inputted to a subject optical fiber, back scattered light of the pulse light from the subject optical fiber is detected by a photodetector to find a Stokes vector, and polarization mode dispersion in a longitudinal direction is measured, the apparatus comprising:
a light source unit for outputting the pulse light having at least three different angular frequencies; and
an arithmetic operation unit for calculating the magnitude of linear polarization components and the magnitude of a circular polarization component of a polarization dispersion vector on the basis of the Stokes vector and thus calculating polarization mode dispersion.

2. The optical fiber characteristics measuring apparatus as claimed in claim 1, wherein the photodetector detects the light intensity from at least three positions in the longitudinal direction of the subject optical fiber and finds a normalized Stokes vector for each position,
the apparatus comprising a birefringence calculating unit for calculating the magnitude of linear polarization components and the magnitude of a circular polarization component of a birefringence vector on the basis of the Stokes vector for each position found by the photodetector and thus calculating the magnitude of birefringence in the subject optical fiber.

3. An optical fiber characteristics measuring apparatus for measuring polarization mode dispersion in a longitudinal direction of a subject optical fiber, the apparatus comprising:
a light source unit for outputting pulse light having at least three different angular frequencies;
a polarization controller for polarizing each pulse light outputted from the light source unit into at least two different polarization states and outputting the polarized pulse light;
a directional coupler for outputting the pulse light polarized by the polarization controller to the subject optical fiber and having back scattered light of the outputted pulse light inputted thereto;
a photodetector for splitting the back scattered light from the directional coupler into polarization states of at least four directions and detecting the light intensity of the back scattered light synchronously with the pulse light outputted from the light source unit, and finding a normalized Stokes vector; and
an arithmetic operation unit for calculating the magnitude of linear polarization components and the magnitude of a circular polarization component of a polarization dispersion vector on the basis of the Stokes vector found by the photodetector and calculating polarization mode dispersion.

4. The optical fiber characteristics measuring apparatus as claimed in claim 1 or 3, wherein the light source unit has:
a continuous light output unit for outputting continuous light having different angular frequencies; and
a pulse generator for converting the continuous light from the continuous light output unit to a desired pulse width and outputting the converted light.

5. The optical fiber characteristics measuring apparatus as claimed in claim 1 or 3, wherein the arithmetic operation unit comprises:

a matrix calculating unit for calculating a Mueller matrix from the normalized Stokes vector for each angular frequency;
a polarization dispersion vector calculating unit for calculating polarization dispersion vectors of back scattered light in accordance with the angular frequencies from the Mueller matrix calculated by the matrix calculating unit;
a linear polarization calculating unit for calculating the magnitude of linear polarization components of a polarization dispersion vector from the polarization dispersion vectors of back scattered light calculated by the polarization dispersion vector calculating unit;
a circular polarization calculating unit for calculating the magnitude of a circular polarization component of the polarization dispersion vector from the difference between the polarization dispersion vectors of back scattered light calculated by the polarization dispersion vector calculating unit; and
a dispersion value calculating unit for calculating a value of polarization mode dispersion from the magnitude of the circular polarization component from the circular polarization calculating unit and the magnitude of the linear polarization components from the linear polarization calculating unit.

6. The optical fiber characteristics measuring apparatus as claimed in claim 3, wherein the photodetector detects the light intensity from at least three positions in the longitudinal direction of the subject optical fiber and finds a normalized Stokes vector for each position,
the apparatus comprising a birefringence calculating unit for calculating the magnitude of linear polarization components and the magnitude of a circular polarization component of a birefringence vector on the basis of the Stokes vector for each position found by the photodetector and thus calculating the magnitude of birefringence in the subject optical fiber.

7. An optical fiber characteristics measuring apparatus in which pulse light is inputted to a subject optical fiber, back scattered light of the pulse light from the subject optical fiber is detected by a photodetector to find a Stokes vector, and birefringence in a longitudinal direction is measured, the apparatus comprising:
a light source unit for outputting the pulse light; and
a birefringence calculating unit for calculating the magnitude of linear polarization components and the magnitude of a circular polarization component of a birefringence vector on the basis of the Stokes vectors of at least three positions and thus calculating the magnitude of birefringence.

8. An optical fiber characteristics measuring apparatus for measuring the magnitude of birefringence in a longitudinal direction of a subject optical fiber, the apparatus comprising:
a light source unit for outputting pulse light;
a polarization controller for polarizing each pulse light outputted from the light source unit into at least two different polarization states and outputting the polarized pulse light;
a directional coupler for outputting the pulse light polarized by the polarization controller to the subject optical fiber and having back scattered light of the outputted pulse light inputted thereto;
a photodetector for detecting the light intensity of the back scattered light from the directional coupler at least at three positions in the longitudinal direction of the subject optical fiber, then detecting the light intensity at least in four directions of different polarization states synchronously with the pulse light, and finding a normalized Stokes vector; and a birefringence calculating unit for calculating the magnitude of linear polarization components and the magnitude of a circular polarization component of a birefringence vector on the basis of the Stokes vector found by the photodetector and calculating the magnitude of birefringence.

9. The optical fiber characteristics measuring apparatus as claimed in claim 7 or 8, wherein the light source unit has:
a continuous light output unit for outputting continuous light; and
a pulse generator for converting the continuous light from the continuous light output unit to a desired pulse width.

10. An optical fiber characteristics measuring apparatus as claimed in one of claims 2 and 6 to 8, wherein the birefringence calculating unit comprises:
a matrix calculating unit for calculating a Mueller matrix from the normalized Stokes vector for each position;
a birefringence vector calculating unit for calculating birefringence vectors of back scattered light in accordance with the positions from the Mueller matrix calculated by the matrix calculating unit;
a linear polarization calculating unit for calculating the magnitude of linear polarization components of a birefringence vector from the birefringence vectors of back scattered light calculated by the birefringence vector calculating unit;
a circular polarization calculating unit for calculating the magnitude of a circular polarization component of the birefringence vector from the difference between the birefringence vectors of back scattered light calculated by the birefringence vector calculating unit; and
a birefringence value calculating unit for calculating the magnitude of birefringence from the magnitude of the circular polarization component from the circular polarization calculating unit and the magnitude of the linear polarization components from the linear polarization calculating unit.

11. An optical fiber characteristics measuring method for measuring polarization mode dispersion in a longitudinal direction of a subject optical fiber, the method comprising:
a step of outputting pulse light having at least three different angular frequencies from a light source unit;
a step of polarizing each pulse light outputted from the light source unit into at least two different polarization states and inputting the polarized pulse light to the subject optical fiber;
a step of splitting back scattered light of the pulse light inputted to the optical fiber into polarization states of at least four directions and detecting the light intensity of the back scattered light synchronously with the pulse light outputted from the light source unit, and finding a normalized Stokes vector for each angular frequency;
a step of calculating the magnitude of linear polarization components and the magnitude of a circular light component of a polarization dispersion vector on the basis of the Stokes vector thus found; and
a step of calculating polarization mode dispersion from the magnitude of the linear polarization components and the magnitude of the circular polarization component of the polarization dispersion vector.

12. The optical fiber characteristics measuring method as claimed in claim 11, further comprising:
a step of detecting the light intensity of the back scattered light from at least three positions in the longitudinal direction of the subject optical fiber synchronously with the pulse light outputted from the light source unit, and finding a normalized Stokes vector for each position;
a step of calculating linear polarization components and a circular polarization component of a birefringence vector on the basis of the Stokes vector for each position thus found, and calculating the magnitude of birefringence in the longitudinal direction of the subject optical fiber; and
a step of calculating birefringence in the subject optical fiber from the magnitude of the linear polarization components and the magnitude of the circular polarization component of the birefringence vector.

13. An optical fiber characteristics measuring method for measuring birefringence in a longitudinal direction of a subject optical fiber, the method comprising:
a step of outputting pulse light from a light source unit;
a step of polarizing each pulse light outputted from the light source unit into at least two different polarization states and inputting the polarized pulse light to the subject optical fiber;
a step of splitting back scattered light of the pulse light inputted to the optical fiber into polarization states of at least four directions and detecting the light intensity of the back scattered light synchronously with the pulse light outputted from the light source unit, and finding a normalized Stokes vector at least at three positions in the longitudinal direction of the subject optical fiber;
a step of calculating linear polarization components and a circular polarization component of a birefringence vector on the basis of the Stokes vector for each position thus found; and
a step of calculating birefringence from the magnitude of the linear polarization components and the magnitude of the circular polarization component of the birefringence vector.

* * * * *